US012061112B2

(12) United States Patent
Weedon et al.

(10) Patent No.: US 12,061,112 B2
(45) Date of Patent: Aug. 13, 2024

(54) DEVICE AND METHOD FOR DETERMINING A MATERIAL COMPOSITION OF A PIPE

(71) Applicant: Viken Detection Corporation, Burlington, MA (US)

(72) Inventors: Hans Weedon, Salem, MA (US); Gilbert W. McKenna, Winthrop, MA (US); Richard Carey, Ashland, MA (US); David Perez, Milford, MA (US); John P. O'Connor, Andover, MA (US)

(73) Assignee: Viken Detection Corporation, Burlington, MA (US)

( * ) Notice: Subject to any disclaimer, the term of this patent is extended or adjusted under 35 U.S.C. 154(b) by 0 days.

(21) Appl. No.: 17/817,975

(22) Filed: Aug. 5, 2022

(65) Prior Publication Data
US 2023/0204410 A1    Jun. 29, 2023

Related U.S. Application Data

(60) Provisional application No. 63/230,522, filed on Aug. 6, 2021.

(51) Int. Cl.
*G01N 27/02*       (2006.01)
*G01B 21/14*       (2006.01)
(Continued)

(52) U.S. Cl.
CPC ........... *G01H 13/00* (2013.01); *G01N 27/025* (2013.01); *G01N 27/028* (2013.01); *G01N 29/12* (2013.01);
(Continued)

(58) Field of Classification Search
CPC ..... E21B 47/09; E21B 47/092; G01D 5/2006; G01H 13/00; G01N 2291/0234;
(Continued)

(56) References Cited

U.S. PATENT DOCUMENTS

| 2,686,039 | A | * | 8/1954 | John | E21B 31/1075 |
| | | | | | 324/333 |
| 2,961,602 | A | * | 11/1960 | John | E21B 47/092 |
| | | | | | 331/65 |

(Continued)

FOREIGN PATENT DOCUMENTS

| DE | 102005045711 A1 | * | 3/2007 | G01B 7/125 |
| KR | 19990017237 A | * | 3/1999 | H05B 6/12 |

(Continued)

OTHER PUBLICATIONS

Electro Scan Inc.: Award-Winning Machine-Intelligent Leak Detection, Leaks Found & Measured in GPM or LPS, Missed by Acoustic Sensors, CCTV Cameras, Fiber Optics, Lasers, and Sonar, https://www.electroscan.com, downloaded on Oct. 5, 2023, 16 pages.

(Continued)

*Primary Examiner* — David L Singer
(74) *Attorney, Agent, or Firm* — Sunstein LLP (57) ABSTRACT

A device, and corresponding method, for determining a presence of lead in a material composition of a pipe includes a probe, a resonant frequency measurement circuit, and a material analyzer. The probe includes an oscillator circuit and can be inserted into an interior cavity of the pipe and emit electromagnetic radiation. The frequency measurement circuit operatively communicates with the oscillator circuit and outputs resonant electromagnetic frequency measurement data indicating a resonant electromagnetic frequency of the oscillator circuit. The material analyzer receives the resonant electromagnetic frequency measurement data, and an additional measurement selected from the group consisting of (i) a measurement of power dissipation of the oscillator circuit and (ii) an interior diameter of the pipe, and outputs a positive or negative indication of whether lead is present in the material composition based on the resonant (Continued)

electromagnetic frequency measurement data and the additional measurement.

18 Claims, 6 Drawing Sheets
(3 of 6 Drawing Sheet(s) Filed in Color)

(51) Int. Cl.
*G01H 13/00* (2006.01)
*G01N 29/12* (2006.01)
*G01N 29/24* (2006.01)
*G01N 33/202* (2019.01)

(52) U.S. Cl.
CPC ......... *G01N 29/2431* (2013.01); *G01B 21/14* (2013.01); *G01N 33/202* (2019.01)

(58) Field of Classification Search
CPC ........... G01N 27/72–725; G01N 29/12; G01N 29/2431; G01N 29/4427; G01N 33/202; G01N 33/20–2028
See application file for complete search history.

(56) References Cited

U.S. PATENT DOCUMENTS

| | | | |
|---|---|---|---|
| 3,090,910 A * | 5/1963 | Moran | G01V 3/28 327/131 |
| 3,862,418 A | 1/1975 | Preiss | |
| 4,365,197 A * | 12/1982 | Pyatt | G01D 9/42 324/221 |
| 4,704,579 A * | 11/1987 | Pyatt | G01N 27/72 324/226 |
| 5,686,674 A | 11/1997 | Lowry et al. | |
| 6,097,785 A | 8/2000 | Elam | |
| 7,839,969 B2 | 11/2010 | Gallup et al. | |
| 9,933,329 B2 | 4/2018 | Hansen et al. | |
| 10,557,772 B2 | 2/2020 | Hansen et al. | |
| 11,085,908 B1 * | 8/2021 | Zamanzadeh | G01N 33/2028 |
| 11,598,714 B1 * | 3/2023 | Zamanzadeh | G01N 17/006 |
| 2001/0019271 A1 * | 9/2001 | Scott | G01N 22/00 324/637 |
| 2006/0289155 A1 * | 12/2006 | Van Kuijk | E21B 47/107 166/249 |
| 2010/0226476 A1 | 9/2010 | Pesce et al. | |
| 2011/0169508 A1 * | 7/2011 | Kohler | G01D 5/2006 324/654 |
| 2013/0105174 A1 * | 5/2013 | Noui-Mehidi | E21B 43/122 166/372 |
| 2016/0230532 A1 * | 8/2016 | Kasperski | G06K 7/10881 |

FOREIGN PATENT DOCUMENTS

| | | | |
|---|---|---|---|
| RU | 2611334 C1 * | 2/2017 | ............. G01B 15/02 |
| WO | WO-7900855 A1 * | 11/1979 | ............. G01N 27/72 |

OTHER PUBLICATIONS

Electro Scan Inc.: Award-Winning Machine-Intelligent Leak Detection, Leaks Found & Measured in GPM or LPS, Missed by Acoustic Sensors, CCTV Cameras, Fiber Optics, Lasers, and Sonar, https://web.archive.org/web/20210826233558/https:/www.electroscan.com, downloaded on Oct. 5, 2023, 7 pages.

The Water Research Foundation: "Evaluation of Lead Pipe Detection by Electrical Resistance Measurement", Project No. 4698, (2020), pp. 1-43.

The Water Research Foundation: "Lead Service Line Identification Techniques", Project No. 4693, (2020), pp. 1-52.

Environmental Protection Agency: "Very Low-Frequency (VLF) Method", Environmental Geophysics, https://archive.epa.gov/esd/archive-geophysics/web/html/very _low-frequency_(vlf )_method.html, May 18, 2016, pp. 1-4.

* cited by examiner

DEVICE AND METHOD FOR DETERMINING A MATERIAL COMPOSITION OF A PIPE

RELATED APPLICATION(S)

This application claims the benefit of U.S. Provisional Application No. 63/230,522, filed on Aug. 6, 2021. The entire teachings of the above application(s) are incorporated herein by reference.

BACKGROUND

It is well known that the presence of lead (Pb) in drinking water causes serious health issues for individuals. Local, state, and federal agencies are working to eliminate lead in the water transport system to remove this health hazard. Many approaches have been researched and developed to provide means to detect lead in pipes to enable removal and replacement of these pipes with other materials such as copper.

SUMMARY

Except for X-ray Fluorescence approaches, the existing techniques have not provided a suitable means to detect the presence of lead repeatably and without the requirement for excavation of the piping under investigation.

Described herein is an electromagnetic device that can determine the material characteristics of metallic tubes or pipes. In particular, the device provides a means reliably to detect lead (Pb) contained in pipes that may be used to transport potable water.

In one embodiment, a device for determining a material composition of a pipe includes:
  a) a probe having an oscillator circuit, the probe being configured to be insertable into an interior cavity of a pipe, the probe being further configured to emit electromagnetic radiation into the interior cavity via the oscillator circuit;
  b) a resonant frequency measurement circuit that is configured to output resonant electromagnetic frequency measurement data indicative of a resonant electromagnetic frequency of the oscillator circuit in an inserted state in which the probe has been inserted into the interior cavity; and
  c) a material analyzer that is configured to receive the resonant frequency measurement data and to output an indication of material composition of the pipe based on the resonant frequency measurement data and an additional measurement.

The additional measurement can be a measurement of power dissipation of the oscillator circuit in the inserted state. The device can further include a current draw circuit that is configured to measure a current draw of the oscillator circuit in order to determine the measurement of power dissipation of the oscillator circuit. The oscillator circuit can further include a magnetic switch that is configured to cause the current draw of the oscillator circuit to increase if the pipe is a galvanized iron pipe.

The additional measurement can be an interior diameter of the pipe. The probe can further include a diameter sensor configured to measure and to output a diameter of the interior cavity of the pipe.

The material analyzer can be configured to use a lookup table to determine the material composition of the pipe based upon the resonant frequency measurement data and the additional measurement.

The material composition can include lead, copper, steel, or galvanized steel, and the material analyzer can be further configured to distinguish the material composition from another material composition.

The device can further include a flexible insertion member having proximal and distal ends, the proximal end configured to be maintained outside of the pipe and the probe configured for attachment to the distal end while the probe emits the electromagnetic radiation into the interior cavity.

The flexible insertion member can further include a marking (e.g., marking 458 in FIG. 4) thereon indicative of an insertion length of the flexible insertion member into the pipe.

The flexible insertion member further can include an encoder (e.g., encoder 460 in FIG. 4) indicative of an insertion length of the flexible insertion member into the pipe.

The device can further include at least one of a probe power supply and probe support electronics attached to the proximal end of the insertion member.

The flexible insertion member can have an outer diameter less than 6.0 inches, less than 1.5 inches, less than 1.0 inch, less than 0.75 inch, or less than 0.5 inch.

The flexible insertion member can include a steering element.

The probe can have an outer diameter less than 6.0 inches, less than 1.5 inches, less than 1.0 inch, less than 0.75 inch, or less than 0.5 inch.

The probe can further include a water level sensor configured to detect a level of water in the pipe.

The device can further include a user interface configured to indicate to a user at least one of an insertion length of the probe into the pipe, a diameter of the interior cavity of the pipe, a level of water in the pipe, and the indication of material composition of the pipe.

The indication of material composition of the pipe can be a positive or negative indication of whether lead is present in the material composition, or an identification of a metal or metal alloy forming a predominant portion of the material composition.

In another embodiment, a method of determining a material composition of a pipe includes:
  a) inserting a probe having an oscillator circuit into an interior cavity of a pipe;
  b) emitting, via the oscillator circuit, electromagnetic radiation into the interior cavity;
  c) determining resonant frequency measurement data indicative of a resonant frequency of the oscillator circuit in an inserted state in which the probe has been inserted into the interior cavity;
  d) analyzing the resonant frequency measurement data and an additional measurement to determine an indication of material composition of the pipe; and
  e) outputting the indication of material composition of the pipe.

The method can utilize or incorporate any of the optional features described above in connection with the embodiment device.

In still another embodiment, a device for determining a material composition of a pipe includes:
  a) means for inserting an oscillator circuit into an interior cavity of a pipe;
  b) means for emitting electromagnetic radiation into the interior cavity via the oscillator circuit;
  c) means for determining resonant frequency measurement data indicative of a resonant frequency of the oscillator circuit in an inserted state in which the oscillator circuit has been inserted into the interior cavity;

d) means for analyzing the resonant frequency measurement data and an additional measurement to determine an indication of material composition of the pipe; and e) means for outputting the indication of material composition of the pipe.

The device can utilize or incorporate further any of the optional features described above in connection with the first-summarized embodiment device.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Described herein is an electromagnetic device that can determine the material characteristics of metallic tubes or pipes. In particular, the device provides a means to detect, reliably, lead (Pb) contained in pipes that may be used to transport potable water.

Figure 1:
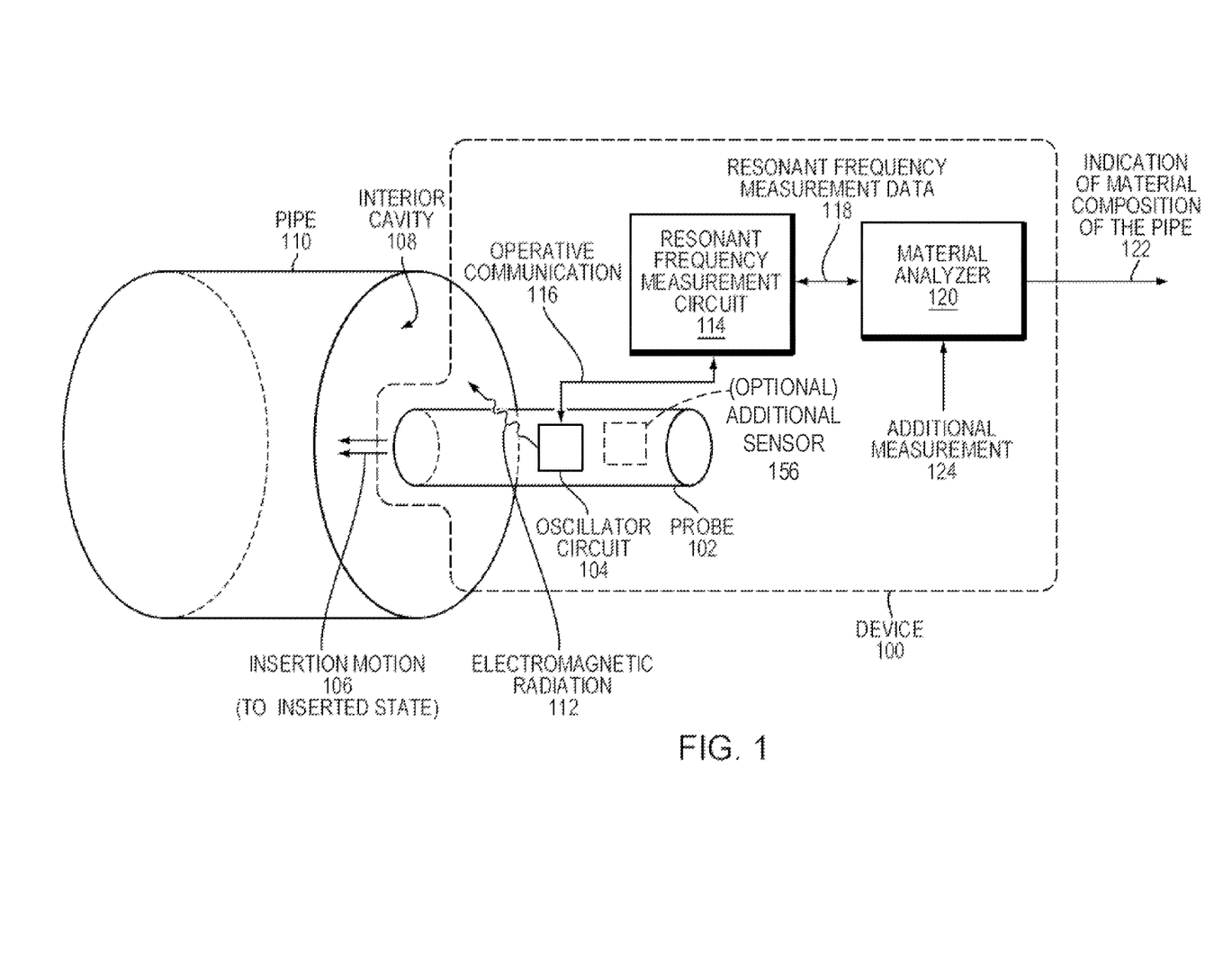
FIG. 1 is a schematic diagram illustrating an embodiment device for determining a material composition of a pipe.

FIG. 1 is a schematic diagram illustrating a device 104 determining a material composition of a pipe 110. The device 100 includes a probe 102 having an oscillator circuit 104. The probe 102 is configured to be insertable into an interior cavity 108 of the pipe 110. The insertability is shown in FIG. 1 by an insertion motion 106. After the insertion motion 106 of the probe 102, at least to an extent needed for the oscillator circuit 104 to be located within the interior cavity 108, the probe 102 may be considered to be in an "inserted state." The probe 102 is further configured to emit electromagnetic radiation 112 into the interior cavity 108 via the oscillator circuit 104.

The device 100 also includes a resonant frequency measurement circuit 114, which is in operative communication 116 with the oscillator circuit 104. The resonant frequency measurement circuit 114 is configured to output resonant electromagnetic frequency measurement data 118 indicative of a resonant electromagnetic frequency of the oscillator circuit 104 in the inserted state in which the probe 102, or a portion thereof including the oscillator circuit 104, has been inserted into the interior cavity 108.

The device 100 further includes a material analyzer 120 that is configured to receive the resonance frequency measurement data 118 and to output an indication 122 of material composition of the pipe 110 based on the resonance frequency measurement data 118 and an additional measurement 124.

Figure 3:
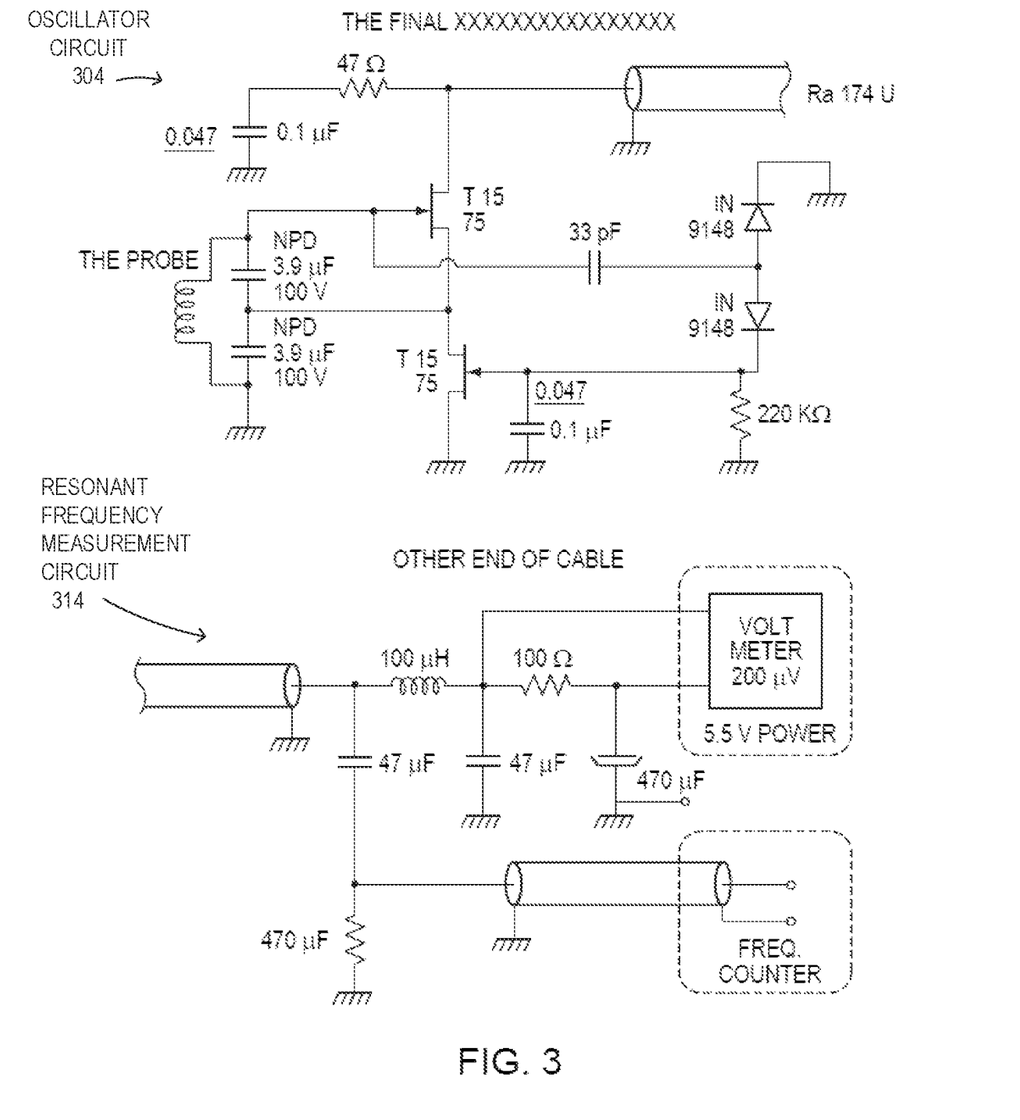
FIG. 3. The circuit design used for the prototype oscillator that was used for testing.

The additional measurement 124 can also be received from the resonant frequency measurement circuit 114 in some embodiments, such as the resonant frequency measurement circuit 314 of the embodiment of FIG. 3. However, in other embodiments, the material analyzer 120 receives and stores the additional measurement 124 in memory, other either via a user inputting the additional measurement 124 through a user interface, via receiving the additional measurements from an optional additional sensor 156, by being pre-stored in memory on the analyzer, or by other means.

Figure 2:
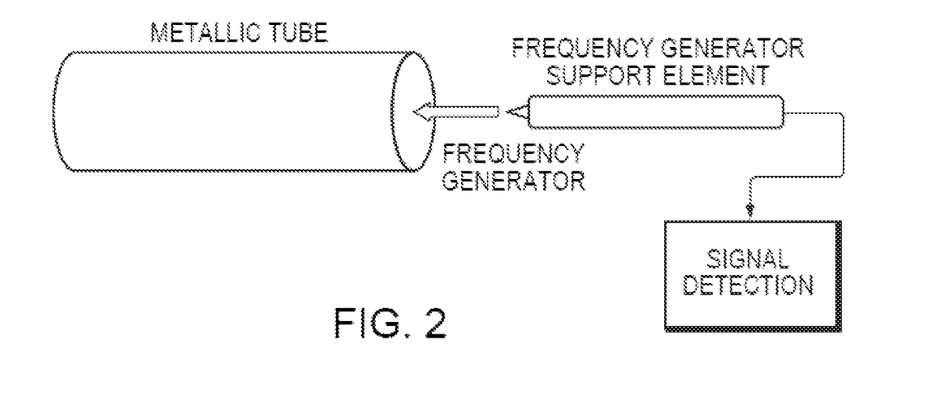
FIG. 2. A schematic showing a frequency generator attached to a support element for pipe inspection.

Many disclosed embodiments use a novel electromagnetic oscillator that can be mounted on a support element (also referred to herein as an "insertion member") that is inserted into the pipe under investigation (FIG. 2). In a preferred embodiment, the support element is flexible, allowing the oscillator to be inserted relatively large distances into pipes that in most instances will not be straight. Since a metallic pipe may be considered as a single-turn waveguide, the application of a frequency will generate a resonance with a frequency that is determined by the electromagnetic inductance of the pipe cavity, which in turn depends on both the diameter of the pipe and the material composition of the pipe. The power dissipated by the oscillator circuit in the pipe cavity also depends on both the diameter and material composition of the pipe, but the dependence on these variables is different than for the resonant frequency.

Viken Detection® investigated two methods of determining the pipe material composition:

First, by measuring just the resonant frequency of the pipe cavity (i.e., inductance of the cavity) and knowing the diameter of the pipe, the material composition of the pipe can be inferred from a look up table. The pipe cavity diameter can be measured separately by some other means, such as via optical, acoustic, or mechanical sensors.

Second, by measuring the resonant frequency of the pipe cavity (i.e., inductance of the cavity) and simultaneously measuring the power dissipation within the pipe cavity, the material composition of the pipe can be directly inferred.

The second approach is preferred, and the inventors have developed an oscillator circuit 304 (FIG. 3) that can simultaneously measure the resonant frequency and the power dissipation of the circuit as it couples to the waveguide, or pipe, via resonant frequency measurement circuit 314. The power dissipation is reflected in the current that the circuit draws, which is converted to a measured voltage across a resistor. The resonant frequency depends strongly on the inner diameter of the pipe, while the dissipated power is determined mostly by the pipe material composition. Copper pipes exhibit low power loss, and lead and galvanized iron pipes exhibit medium power loss.

Figure 4:
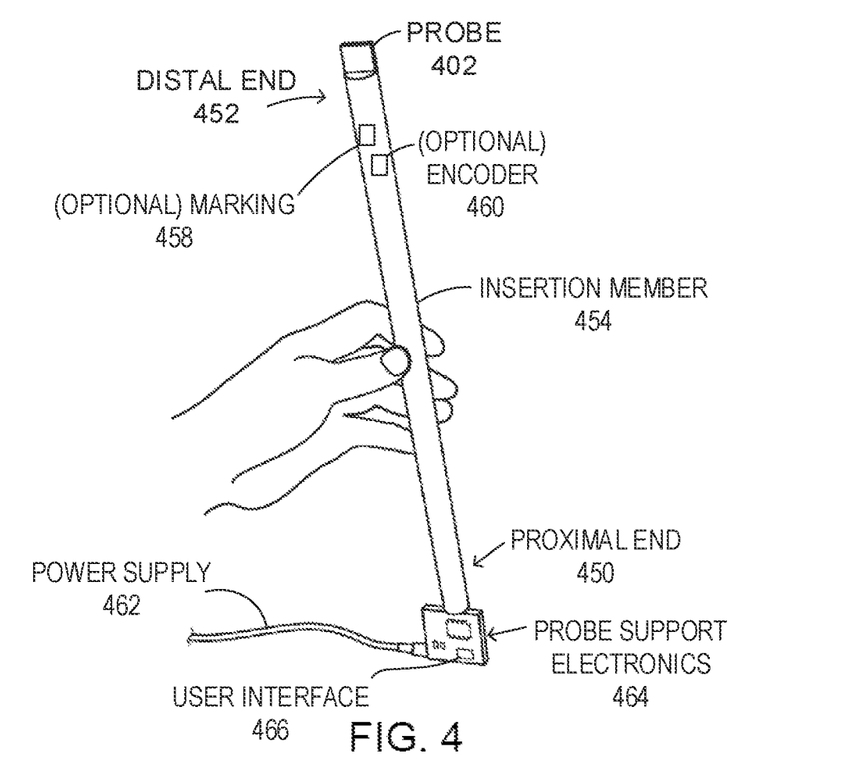
FIG. 4. A photo showing the support element and frequency oscillator.

Testing has been performed by the inventors on new, unused pipes using an embodiment, proof-of-concept probe and oscillator circuit (FIG. 4). For each candidate pipe sample, the power dissipation or current draw of the circuit (measured in mV) and the resonant frequency of the pipe (measured in kHz) was recorded, and the results are plotted in FIG. 5.

Figure 5:
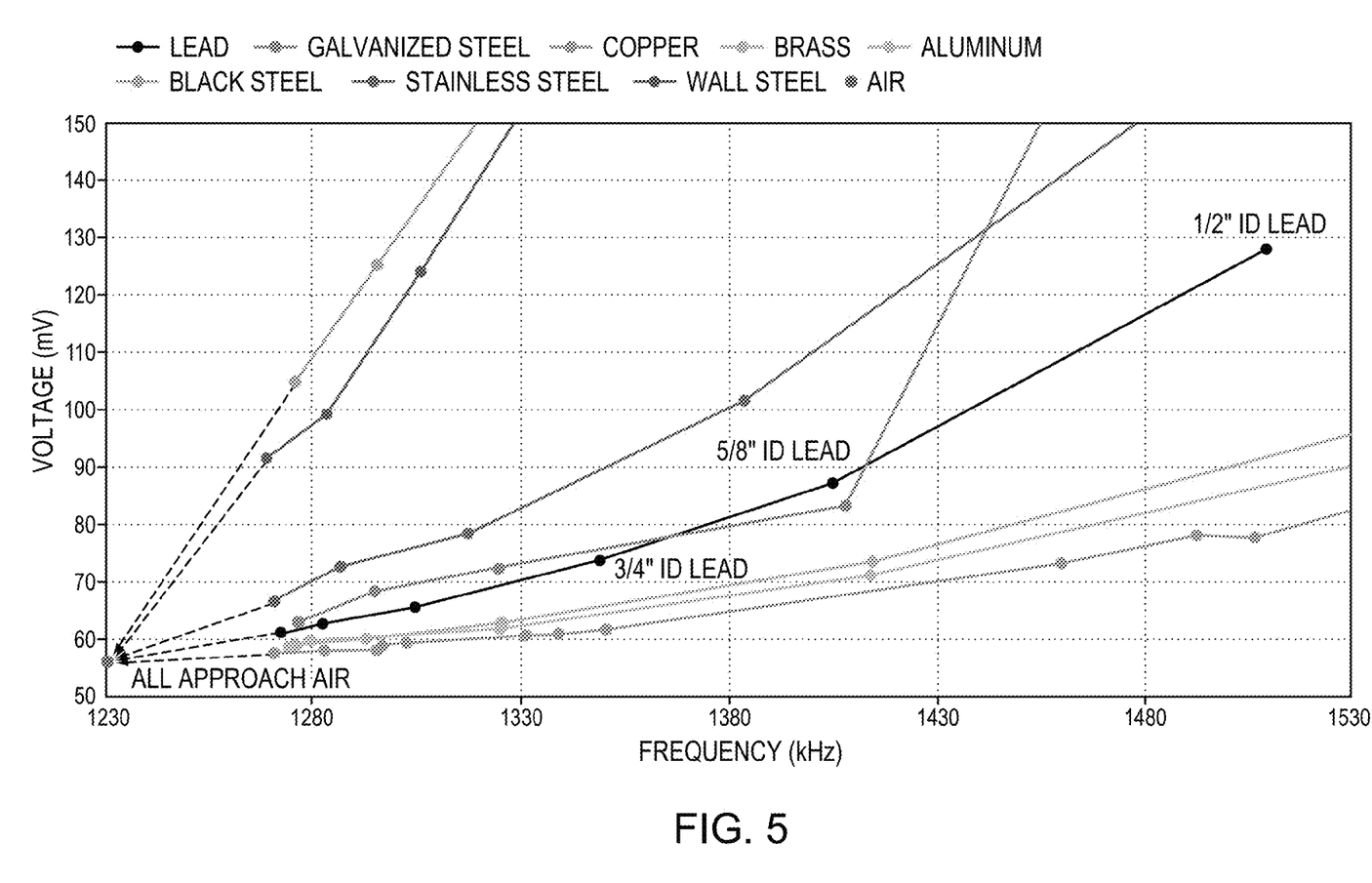
FIG. 5. A plot of power dissipation (measured in mV) vs. resonant frequency (measured in kHz) for various new and unused pipe candidates that were tested.

The technique clearly separates lead pipes of all diameters (black circles) from pipes with other material compositions, except for galvanized steel pipes (orange circles). However, the inventors have discovered that discriminating galvanized steel pipes from lead pipes can be done by adding a magnetic switch that induces an additional current draw for galvanized steel pipes. With this modification, a pipe of a given diameter will induce a low current draw for copper pipes, an intermediate current draw for lead pipes, and a high current draw for galvanized steel pipes.

Figure 6:
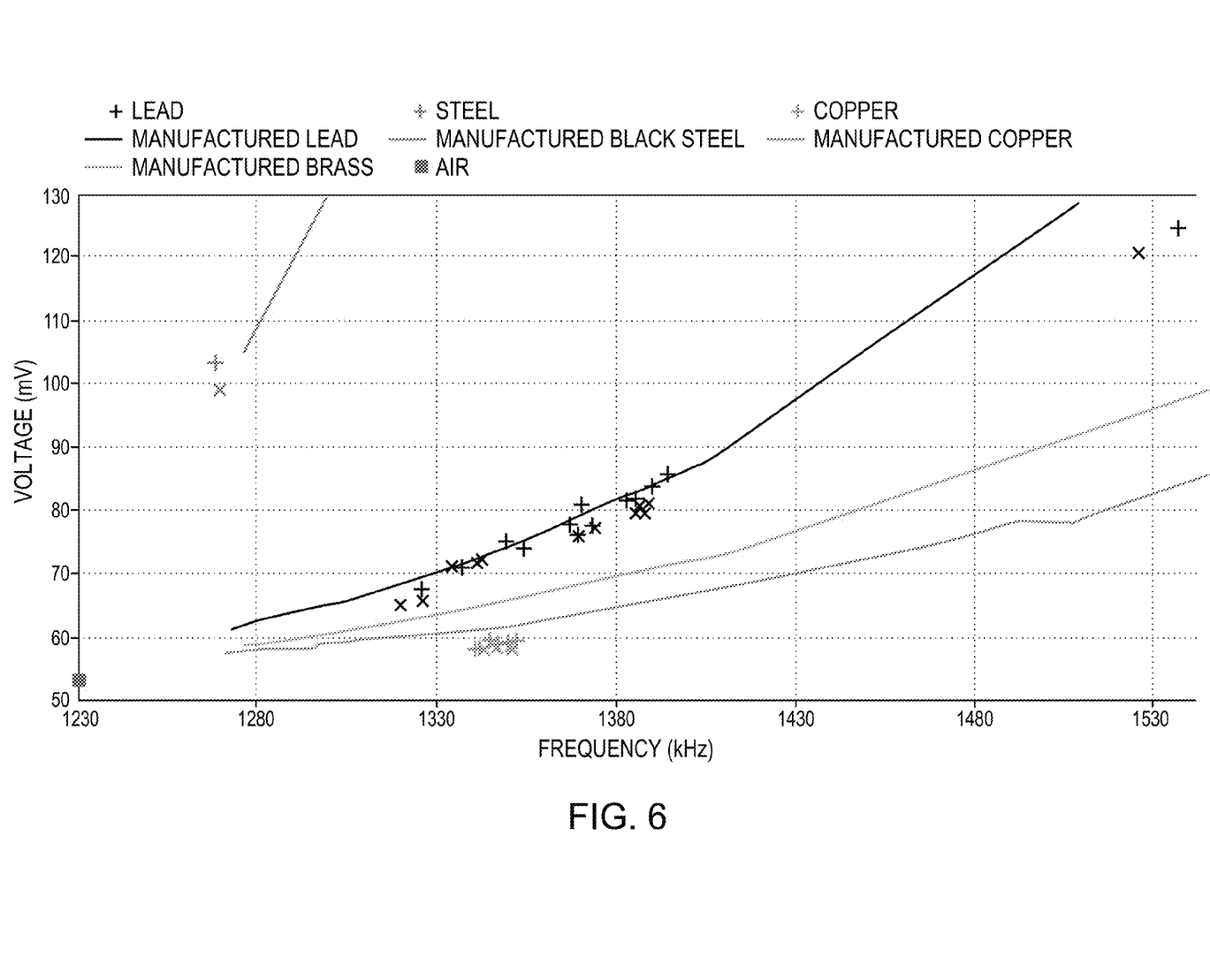
FIG. 6. A plot of power dissipation (measured in mV) vs. resonant frequency (measured in kHz) for various used lead, copper, and steel pipe candidates that were tested.

Additional testing has been performed by the inventors on pipes that had previously been buried underground for many years from old apartment buildings located in the Boston area. The measurements obtained with the old copper, iron, and lead pipes are shown using a cross symbol in FIG. 6, overlaid on the lines representing the prior measurements obtained with the unused pipes. The lead pipes remain well separated from the other pipes, apart from the larger diameter brass pipes, which may need to be removed regardless, due to the relatively high lead content (approximately 8%) found in older brass pipes and fittings.

Figure 7:
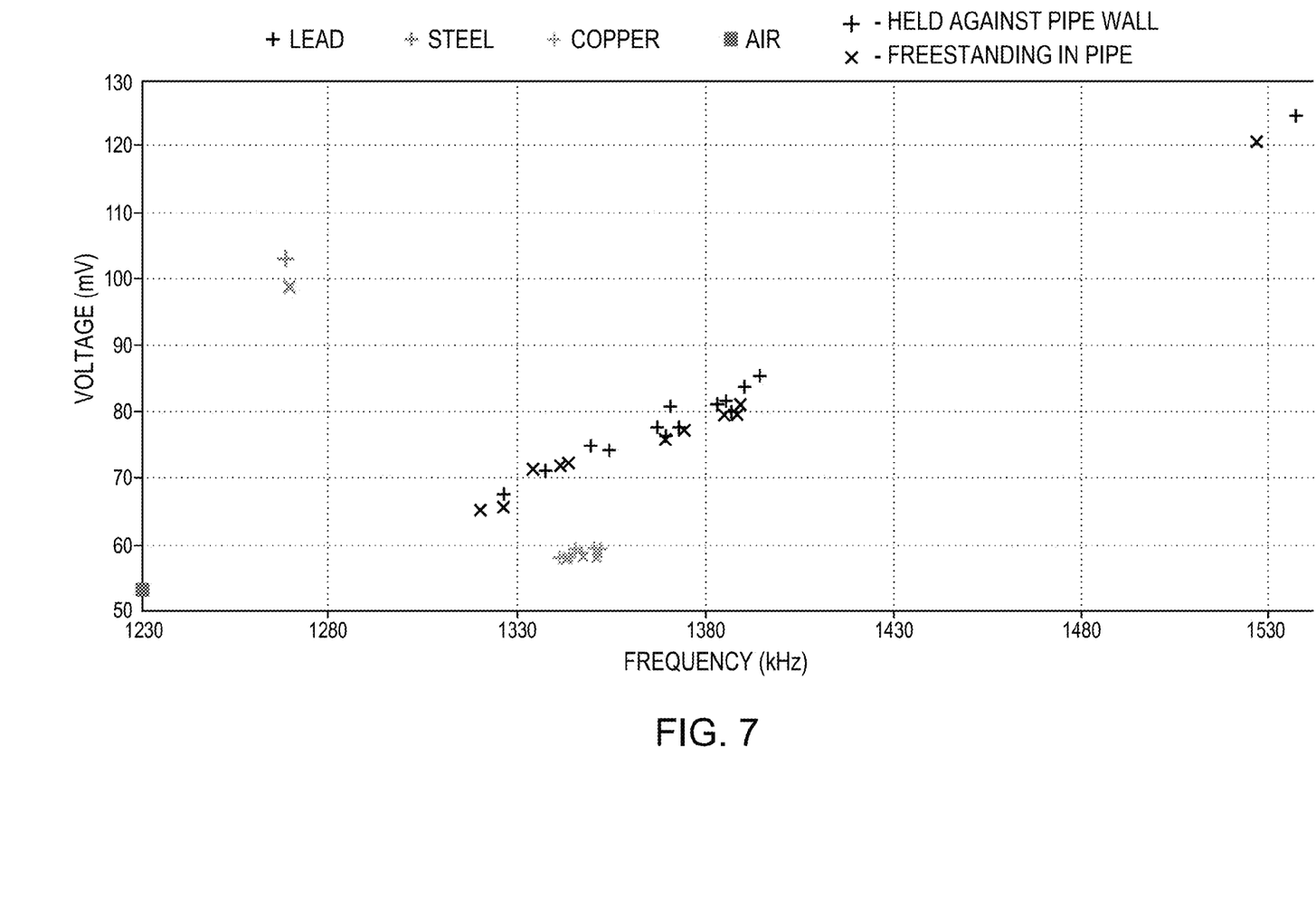
FIG. 7. A plot of power dissipation (measured in mV) vs. resonant frequency (measured in kHz) for various lead pipes, with the frequency probe held against the inside wall of the pipes and with the probe free-standing inside the pipe.

It was also confirmed that the measurements are quite insensitive to the precise location of the probe within the interior of the pipe. This is shown in FIG. 7 for lead pipes, where the probe was held tightly against the wall (+ symbol), versus the probe being unconstrained within the pipe interior (x symbol). In both cases the measured values do not deviate to a large degree from the trend line shown in FIG. 4 and FIG. 5 for lead pipes.

As shown in FIG. 4, the proof-of-concept device includes a probe 402 and oscillator circuit (FIG. 4) attached to the distal end 452 of an insertion member 454. The probe 402 is inserted into the pipe to a specified distance, which can be indicated, and due to the nature of the pipe as a resonant cavity, a distinct resonance frequency will be generated that depends on the cavity inductance, which is function of both the pipe diameter and the pipe material composition.

A first embodiment of the invention uses the measured resonant frequency and the known diameter of the pipe (measured via some additional means, such as using an auxiliary optical, acoustic, or mechanical sensor of some type). A lookup table (LUT) can then be used with the resonant frequency (measured in kHz) and the pipe diameter (measured, for example, in mm) as the two input parameters, with the return value being the pipe composition material. The LUT return value can also specify an associated degree of confidence on the returned pipe material composition, depending on exactly where in the mm/kHz space the measurements lie. This information can then be presented to the operator on a small display screen on the proximal end 450 of the insertion member.

A second embodiment relies on the energy dissipated by the oscillator circuit, which depends strongly on the pipe composition. The energy loss is reflected in the current draw of the circuit and simultaneously measured as a voltage along with the resonant frequency, as described previously. An additional current draw is introduced by the magnetic switch in the presence of any galvanized steel that may be contained within the pipe, ensuring that the current draw for galvanized steel pipes is always higher than for non-magnetic lead pipes. A lookup table (LUT) can then be used with the resonant frequency (measured in kHz) and the current draw (measured across a resistor in mV) as the two input parameters, with the return value being the pipe composition material. The LUT return value can also specify an associated degree of confidence on the returned pipe material composition, depending on exactly where in the mV/kHz space the measurements lie. This information can then be presented to the operator on a small display screen on the proximal end of the insertion member.

For commercially available units, the oscillator probe would be attached to the distal end of a hollow flexible shaft composed of Delrin, nylon, or other appropriate plastic material. The outer diameter of the support element would be selected to be close to, but slightly under, the inner diameter of the pipes to be measured, ensuring that the oscillator probe is placed approximately at the center of the pipe.

Alternate embodiments of the device include a steering element in the insertion member, which allows the operator to steer the tip of the member containing the probe around corners or obstructions during the insertion process. Installing an optical camera and light source onto the probe would allow a visual image to be displayed to the operator, assisting them in guiding the probe during the insertion process.

An electronics module that contains the power supply and support electronics can be attached at the proximal (or operator) end of the insertion member. Electrical cables supplying power and data communications to and from the probe can be routed through the interior of the hollow, flexible insertion member. A user interface connected to the support electronics can allow data and optical images to be presented to the operator in real time in certain embodiments.

Further embodiments of the device can include auxiliary sensors to measure the interior diameter of the pipe, such as optical, acoustic, or mechanical sensors. An additional sensor that indicates the water level inside the interior of the pipe can also be located in the probe. This sensor can be based on the electrical conductivity measured between two conductors located on the outside of the probe.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A device for determining a presence of lead in a material composition of a pipe, the device comprising:
   a probe having an oscillator circuit, the probe being configured to be insertable into an interior cavity of a pipe, the probe being further configured to emit electromagnetic radiation into the interior cavity via the oscillator circuit;
   a resonant frequency measurement circuit that is configured to output resonant electromagnetic frequency measurement data indicative of a resonant electromagnetic frequency of the oscillator circuit in an inserted state in which the probe has been inserted into the interior cavity; and
   a material analyzer that is configured to receive the resonant electromagnetic frequency measurement data and to output a positive or negative indication of whether lead is present in the material composition of the pipe based on the resonant electromagnetic frequency measurement data and an additional measurement selected from the group consisting of (i) a measurement of power dissipation of the oscillator circuit in the inserted state and (ii) an interior diameter of the pipe.

2. The device of claim 1, wherein the additional measurement is the measurement of power dissipation of the oscillator circuit in the inserted state.

3. The device of claim 2, further including a current draw circuit that is configured to measure a current draw of the oscillator circuit in order to determine the measurement of power dissipation of the oscillator circuit.

4. The device of claim 1, wherein the additional measurement is the interior diameter of the pipe.

5. The device of claim 4, wherein the probe further includes an additional sensor configured to measure and to output the interior diameter of the pipe.

6. The device of claim 1, wherein the material analyzer is configured to use a lookup table to determine the presence of lead in the material composition of the pipe based upon the resonant electromagnetic frequency measurement data and the additional measurement.

7. The device of claim 1, wherein the material composition includes lead, copper, steel, or galvanized steel, and wherein the material analyzer is further configured to distinguish the material composition from another material composition.

8. The device of claim 1, further including a flexible insertion member having proximal and distal ends, the proximal end configured to be maintained outside of the pipe and the probe configured for attachment to the distal end while the probe emits the electromagnetic radiation into the interior cavity.

9. The device of claim 8, wherein the flexible insertion member further includes a marking thereon indicative of an insertion length of the flexible insertion member into the pipe.

10. The device of claim 8, wherein the flexible insertion member further includes an encoder indicative of an insertion length of the flexible insertion member into the pipe.

11. The device of claim 8, further including at least one of a probe power supply and probe support electronics attached to the proximal end of the insertion member.

12. The device of claim 8, wherein the flexible insertion member has an outer diameter less than 6.0 inches, less than 1.5 inches, less than 1.0 inch, less than 0.75 inch, or less than 0.5 inch.

13. The device of claim 1, wherein the probe has an outer diameter less than 6.0 inches, less than 1.5 inches, less than 1.0 inch, less than 0.75 inch, or less than 0.5 inch.

14. The device of claim 1, wherein the probe further includes a water level sensor configured to detect a level of water in the pipe.

15. The device of claim 1, further including a user interface configured to indicate to a user at least one of an insertion length of the probe into the pipe, a diameter of the interior cavity of the pipe, a level of water in the pipe, and the indication of whether lead is present in the material composition of the pipe.

16. The device of claim 1, wherein the indication of whether lead is present in the material composition of the pipe includes an identification of a metal or metal alloy forming a predominant portion of the material composition.

17. A method of determining a presence of lead in a material composition of a pipe, the method comprising:
   inserting a probe having an oscillator circuit into an interior cavity of a pipe;
   emitting, via the oscillator circuit, electromagnetic radiation into the interior cavity;
   determining resonant electromagnetic frequency measurement data indicative of a resonant electromagnetic frequency of the oscillator circuit in an inserted state in which the probe has been inserted into the interior cavity;
   analyzing the resonant electromagnetic frequency measurement data and an additional measurement, selected from the group consisting of (i) a measurement of power dissipation of the oscillator circuit in the inserted state and (ii) an interior diameter of the pipe, to determine a positive or negative indication of whether lead is present in the material composition of the pipe; and
   outputting the positive or negative indication of whether lead is present in the material composition of the pipe.

18. A device for determining a presence of lead in a material composition of a pipe, the device comprising:
   means for inserting an oscillator circuit into an interior cavity of a pipe;
   means for emitting electromagnetic radiation into the interior cavity via the oscillator circuit;
   means for determining resonant electromagnetic frequency measurement data indicative of a resonant electromagnetic frequency of the oscillator circuit in an inserted state in which the oscillator circuit has been inserted into the interior cavity;
   means for analyzing the resonant electromagnetic frequency measurement data and an additional measurement, selected from the group consisting of (i) a measurement of power dissipation of the oscillator circuit in the inserted state and (ii) an interior diameter of the pipe, to determine a positive or negative indication of whether lead is present in the material composition of the pipe; and
   means for outputting the positive or negative indication of whether lead is present in the material composition of the pipe.

* * * * *